United States Patent [19]
Richards et al.

[11] Patent Number: 5,629,081
[45] Date of Patent: May 13, 1997

[54] PREMOISTENED, FLUSHABLE, DISPOSABLE AND BIODEGRADABLE WET WIPES

[75] Inventors: Marc F. Richards, Dover, Del.; Kenneth Y. Wang, West Chester, Pa.

[73] Assignee: Kimberly-Clark Tissue Corporation, Neenah, Wis.

[21] Appl. No.: 414,540

[22] Filed: Mar. 31, 1995

[51] Int. Cl.$^6$ .................................................. D04H 1/58
[52] U.S. Cl. ..................... 442/96; 424/404; 424/408; 442/118; 442/123
[58] Field of Search .................................. 428/245, 288, 428/289, 290; 424/404, 408

[56] References Cited

U.S. PATENT DOCUMENTS

| | | | |
|---|---|---|---|
| 3,689,314 | 9/1972 | Duchane | 117/140 |
| 3,808,165 | 4/1974 | Duchane | 260/29.6 |
| 3,881,210 | 5/1975 | Drach et al. | 15/104.93 |
| 4,309,469 | 1/1982 | Varona | 428/74 |
| 4,343,133 | 8/1982 | Daniels et al. | 53/431 |
| 4,990,334 | 2/1991 | Longino et al. | 424/401 |
| 5,252,332 | 10/1993 | Goldstein | 424/402 |
| 5,256,417 | 10/1993 | Koltisko | 424/402 |

FOREIGN PATENT DOCUMENTS

0003186A1  7/1979  European Pat. Off. ......... D04H 1/64

OTHER PUBLICATIONS

Patent Abstracts of Japan, vol. 018, No. 647 (C–1283), 8 Dec. 1994 & JP,A,06248548 (Kuraray Co. Ltd.), 6 Sep. 1994, see abstract.

*Primary Examiner*—Marion E. McCamish
*Assistant Examiner*—Elizabeth M. Cole
*Attorney, Agent, or Firm*—Jeffrey B. Curtin

[57] ABSTRACT

The present invention provides a pre-moistened, dispersible, and biodegradable wet wipe comprising a web of nonwoven fibers contacted with a PVOH containing binder. The binder-contacted web further comprises an aqueous lotion solution comprising from about 0.1 to about 0.9 percent by weight of the lotion of boric acid and from about 5 to about 8 percent by weight of the lotion of an alkali metal bicarbonate. The resulting wet wipe has a pH between 7 and about 9 and a wet strength between about 8 and about 20 oz/in.

10 Claims, 3 Drawing Sheets

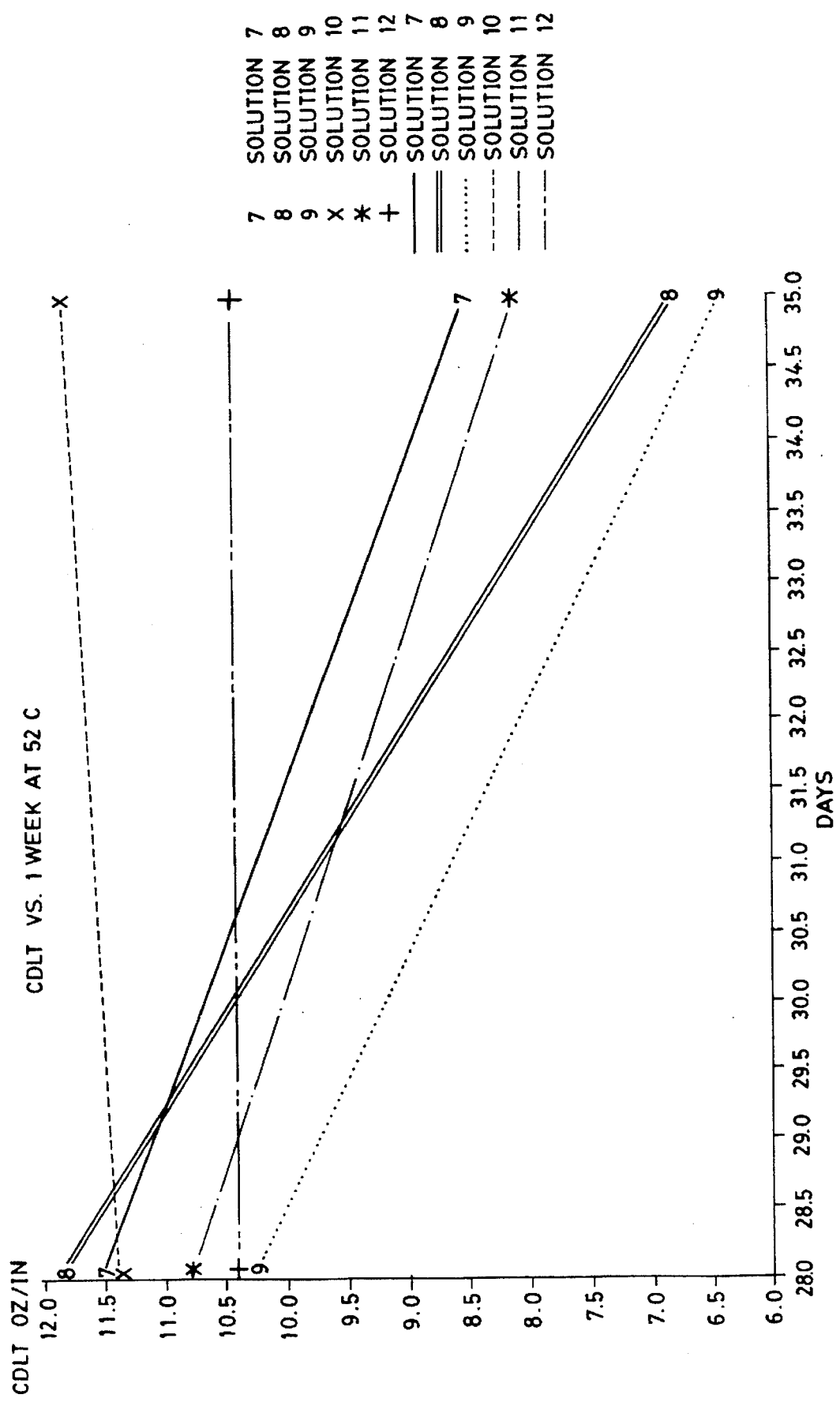

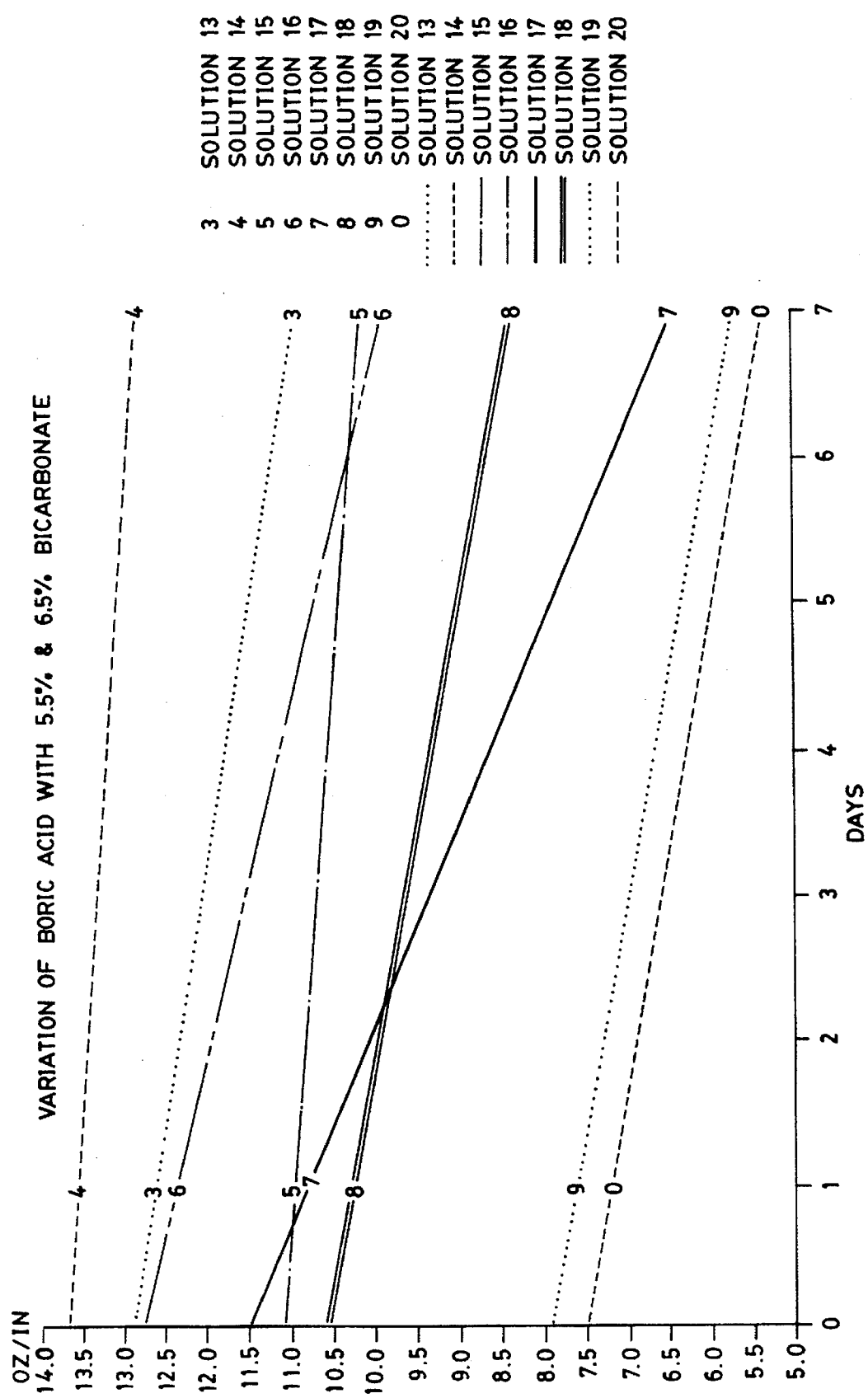

PREMOISTENED, FLUSHABLE, DISPOSABLE AND BIODEGRADABLE WET WIPES

FIELD OF THE INVENTION

This invention relates to personal care, premoistened, cleansing wet wipes that can be used and disposed discreetly and safely by flushing down the toilet bowl.

BACKGROUND OF THE INVENTION

Pre-moistened, skin cleansing tissues are well known commercially and are referred to as wet wipes, towelettes, and the like. These tissues may be prepared from paper or paper products which are treated in such a manner so as to improve their wet strength. Such tissues are generally sized such that they are useful for use as a wash cloth, and may be packaged in closed containers. Alternatively, the tissues may be individually packaged.

Wet wipe tissues are generally treated with an aqueous alcohol solution in order to maintain moistness. The tissues may also comprise a surface active detergent, humectant, and a scenting agent or fragrance.

Numerous wet wipe like materials have been described. U.S. Pat. No. 3,808,165 describes a process for preparing a wet wipe in which boric acid is added to polyvinyl alcohol (PVOH) rather than adding the boric acid to the lotion at a later time. The web is dried, the heat of drying breaking down the organic acids present which raises the pH to stabilize the binder. Sodium bicarbonate is not used to raise the pH.

U.S. Pat. No. 3,881,210 describes a sanitary wiper comprising a PVOH central layer, wherein the multilayered structure is bonded together by means of embossing roll with a land area of 4 to 25%. However, no stabilizing ingredients, percentages, nor strength criteria are specified.

U.S. Pat. No. 4,309,469 describes a wipe which is bonded with a three part adhesive binder consisting of PVOH and a self-crosslinking thermosetting polymer and a non-self-crosslinking thermosetting polymer. The complexing agent is alpha hydroxy and O-aromatic hydroxy acids rather than boric acid and sodium bicarbonate.

U.S. Pat. No. 4,343,133 describes a polyvinyl acetate latex impregnated towelette, which uses a high percentage of boric acid, at least 3%, which is much too harsh for many applications. This towelette also does not comprise sodium bicarbonate.

U.S. Pat. No. 5,256,417 describes a water dispersible towelette which is impregnated with non-aqueous lotion formulations. The non-aqueous lotion composition of organic compound stabilizes the PVOH binder but does not dissolve PVOH.

U.S. Pat. No. 3,689,314 uses a different process to prepare flushable wrappers for absorbent pads. The PVOH binder and the chemical additives are added together and dried. Heat causes the chemicals to react and render the binder sufficiently strong in the condition of use. The environment of the absorbent pad is a very small zone exposure of low level of saturation of the body fluids. The time of exposure is also limited to a few hours, rather than months. In addition, heating is required for crosslinking after the borax is formed. Furthermore, less than 0.5% sodium bicarbonate is used.

A major concern of many of these existing tissues, which use a flushable binder system containing boric acid, is that boric acid in high dosage can cause toxic skin irritation, particularly in individuals with compromised skin. Thus, there is a need to provide a gentle lotion system containing low concentrations of boric acid. In addition, all of the wet wipes currently in the marketplace have an acidic pH. The most common range is from a pH of 4.0 to 5.5. The skin's pH is about 5.5 in adults and babies, which is the pH most manufacturers try to achieve when developing pH-balanced products.

U.S. Pat. No. 5,252,332 describes a premoistened, flushable towelette impregnated with polyvinyl alcohol-containing binders. A PVOH based binder is applied to the non-woven web, which is lotionized with a lotion containing boric acid and sodium bicarbonate. The sodium bicarbonate range is stated to be 0.2 to 3%. In addition, the towelette contains an undesirably high quantity of boric acid. The borate to bicarbonate ratio is 4:1 to 1:4, and is preferably 2:1 to 1:2. Moreover, the towelette is susceptible to growth of microorganisms, especially mold, and is therefore not appropriate for long-term storage. In contrast, Applicants' invention provides a borate to bicarbonate ratio of 1:8.5 to 1:12 and provides a far superior wet strength.

Applicants' invention provides a number of features which are desired but not found in the prior art. First, Applicants' invention provides unexpected higher wet strength that are unavailable in other formulations with similar needs. Second, it provides for a high percentage of sodium bicarbonate which enhances cleansing and deodorizing, while providing an alkaline pH suitable for babies and infants. Finally, Applicants' invention is surprisingly compatible with existing BABY FRESH™ lotion system, synergistically making a gentle and efficacious cleansing wipe which is also flushable, dispersible and biodegradable. Applicants' invention provides for the first lotionized wet wipe having an alkaline pH, high wet strength, low boric acid concentrations that provide mildness, and a preservative system providing for long-term storage. Moreover, Applicants' invention surprisingly provides a wet wipe having an alkaline pH while simultaneously being mild and gentle.

The present invention provides a personal care, premoistened, cleansing wet wipe comprising a PVOH containing binder in contact with an aqueous solution containing borate and bicarbonate ions. The towelette exhibits desirable wet tensile strength but rapid disintegration in water. This material is used as a flushable, dispersible and biodegradable wet wipe for babies, kids, teens and adults of both male and female of all ages. Applicants' wet wipe can be disposed discreetly by flushing down the toilet bowl safely. The product also meets aerobic and anaerobic biodegradation existing in sewer and septic systems. Applicants' invention further comprises a mild binder and lotion system that allows the wet wipe to disperse into very small fibrous components under conditions of volumes and velocity of the water in which the wipe is placed.

SUMMARY OF THE INVENTION

The present invention relates to a pre-moistened, dispersible, and biodegradable wet wipe comprising a non-woven web of fibers contacted with a PVOH containing binder. The binder can be either a polyvinyl alcohol, an aqueous polyvinyl alcohol stabilized polymer emulsion, a blend of a polyvinyl alcohol or an aqueous polymer emulsion or a combination thereof. The binder-contacted web further comprises an aqueous lotion solution comprising from about 0.1 to about 0.9 percent by weight of the lotion of boric acid and from about 5 to about 8 percent by weight of the lotion of an alkali metal bicarbonate. The resulting wet wipe has a pH between 7 and about 9 and a wet strength between about 8 and about 20 oz/in.

The present invention relates to a pre-moistened, dispersible, and biodegradable wet wipe comprising a non-woven web of fibers contacted with a PVOH containing binder. The binder can be either a polyvinyl alcohol, an aqueous polyvinyl alcohol stabilized polymer emulsion, a blend of a polyvinyl alcohol or an aqueous polymer emulsion or a combination thereof. The wet wipe also comprises an aqueous lotion solution comprising from about 0.3 to about 0.7 percent by weight of the lotion of boric acid and from about 6 to about 7 percent by weight of the lotion of sodium bicarbonate, and further comprising propylene glycol, cocoamphodiacetate, polysorbate 20, methyl paraben, propyl paraben, and SUTTOCIDE A™ (sodium hydroxymethylglycinate) antimicrobial . The resulting wet wipe has a pH between 7 and about 9 and a wet strength between about 12 and about 16 oz/in.

BRIEF DESCRIPTION OF THE DRAWINGS

FIG. 2 depicts CDLT values vs. time over one week at 52° C. for wet wipes comprising lotion compositions 7–12 having various boric acid/sodium bicarbonate concentrations. The lotion compositions are shown in Table 1.

FIG. 3 depicts CDLT values vs. time over one week at room temperature for wet wipes comprising lotion compositions 13–20 having various boric acid/sodium bicarbonate concentrations. The lotion compositions are as follows (% boric acid/% sodium bicarbonate): 13=0.99%/5.5%; 14=0.99%/6.5%; 15=0.66%/5.5%; 16=0.66%/6.5%; 17=0.33%/5.5%; 18=0.33%/6.5%; 19=0.11%/5.5%; and 20=0.11%/6.5%.

DETAILED DESCRIPTION OF THE PREFERRED EMBODIMENTS

Figure 1:
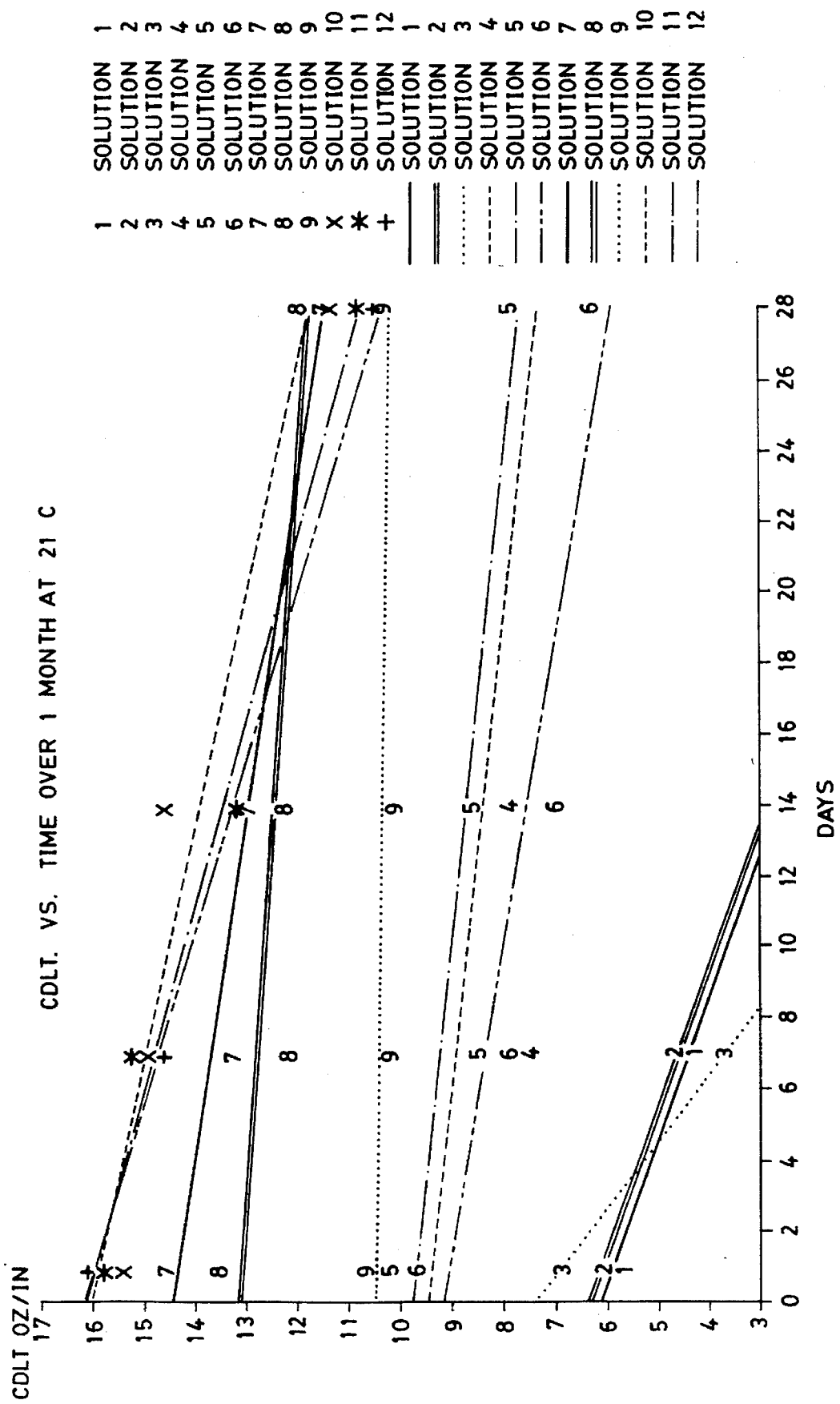
FIG. 1 depicts cross-directional lotionized tensile CDLT) values vs. time over one month at room temperature for wet wipes comprising lotion compositions 1–12 having various boric acid/sodium bicarbonate concentrations. The lotion compositions are shown in Table 1.

The present invention relates to a non-woven wet wipe product that is both safe to use and also flushes and disperses and finally biodegrades in the appropriate environments. This material is used as a flushable, dispersible and biodegradable wet wipe for both male and female babies, kids, teens and adults of all ages. The wet wipe of the invention has an alkaline pH but yet retains mildness and gentleness allowing its use in applications for children and infants.

As used herein, the term "wet wipe" is meant to refer to a non-woven web of fibers that can be used for cleansing purposes. The wet wipe can also be referred to as a towelette.

As used herein, the term "dispersible" is meant to refer to the breaking apart of the wet wipe in water or other liquid solutions.

As used herein, the term "percent by weight" is meant to refer to the quantity by weight of a compound in the lotion of the wet wipe as a percentage of the weight of the lotion.

In its basic form, the wet wipe of the invention consists of a non-woven fibrous material, bonded with a PVOH system and lotionized with a non-irritating formula containing very low levels of boric acid and a moderate level of sodium bicarbonate. The wet wipe is composed primarily of cellulose wood pulp fibers with an added amount of textile fibers to enhance wet and dry strength. It is preferred that the wood pulp fibers comprise about 75% to about 95% and the textile fibers comprise about 5% to about 25% of the wet wipe. It is more preferable that the wood pulp fibers comprise about 85% to about 90% and the textile fibers comprise about 10% to about 15% of the wet wipe. The preferred textile fibers include rayon, cotton, wool, acetate or tencel fibers.

The art skilled will readily have the knowledge necessary to procuce a web of fibers capable of being used as a wet wipe. Those skilled in the art of non-woven materials will readily appreciate that a web of fibers can be formed by carding, by wet laying, by spunbonding, as well as by melt blowing. Moreover, these processes can be combined to achieve unique results. The homogeneous air laid structure that is preferred offers the most desirable and economical version for this application.

The non-woven web of the wet wipe is formed preferably by the airlaid process, where all fibers are intimately blended rather than layered, to achieve a high degree of blend homogeneity as well as high specific volume. The airlaid web is compressed and can be embossed with a pattern. Embossing can produce wet wipe products having a variety of words, pictures, or the like, such as, for example, animals, dollshapes, and the like. The airlaid web is sprayed on both sides with a PVOH binder so that a low level of solids add-on of about 2% to about 20% is applied. It is preferred that a solids add-on of about 5% to about 10% is applied. The binder is typically in a 30% solids solution, preblended, and ready to dilute to a 10% solution which can be applied at about 100% wet pick up, to get a 10% binder add-on.

The web is air dried and wound on a roll. The web is slit, folded, pre-moistened with lotion, cut and stacked into a tub. The lotion saturation is about 100% to about 350% saturation. It is more preferable that the lotion saturation is about 250% to about 350% saturation. The basis weight of the web (dry weight) is about 70 grams/square meter. The wet thickness of the product is about 20 to about 25 mils (1 mil=1/1000 of an inch). Existing wet wipe products include Kid KID FRESH™ not wipes and SOFKINS™ wet wipes.

The PVOH containing binders of the present invention include PVOH, an aqueous PVOH stabilized polymer emulsion, a blend of a PVOH and an aqueous polymer emulsion or a combination thereof. The preferred binder is the Air Products A-911 PVOH binder.

The lotion formulation comprises water, a low level of boric acid, preferably from about 0.1 to about 0.9 percent by weight of the lotion, and a moderate level of an alkali metal bicarbonate, preferably from about 5 to about 8 percent by weight of the lotion, making it a very gentle lotion. The lotion more preferably comprises from about 0.3 to about 0.7 percent by weight of the lotion of boric acid and from about 6 to about 7 percent by weight of the lotion of an alkali metal bicarbonate. The alkali metal bicarbonate is preferably sodium bicarbonate. The boric acid and sodium bicarbonate are mixed in the lotion solution, rather than in the binder mix.

The lotion formulation also comprises a preservative system. Current commercial preservative systems are designed for acidic wet wipes. Therefore, an alkaline lotion formulation comprising a preservative system provides several advantages including protection against microorganisms and long-term storage. It is preferred that the preservative provide anti-microbial activity including anti-bacterial activity, anti-fungal activity or anti-yeast activity, or a combination thereof. It is also preferred that the preservative provide the wet wipe of the invention the ability to be stored for as long as three years. Preferred preservatives include formaldehyde and formaldehyde donors, glutaraldehyde, quaternium-15, imidazolidinyl and diazolidinyl urea, parabens, chloroxylenol, chlorothymol, triclosan, propamidine isethionate, dibromopropamide, hexaminidine, isethionate, zinc pyrithione, oxadine A, kathon, alkyltrimethylammonium bromide, benzalkonium chloride, bezethonium chloride, piroctone olamine, glyceral monolaurate, or a combination thereof. The preservative generally comprise from about 0.01 to about 1.5 percent by weight of the lotion.

The lotion formulation can also comprise moisturizing and/or emollient agents, surfactants and/or emulsifiers, and fragrances. Preferred moisturizers and emollients include polyols, proteins, plant derivatives, and water soluble barrier forming materials, such as, for example, lanolins, fatty acids, alcohols, and the like, or a combination thereof. The moisturizers and emollients generally comprise from about 0.1 to about 10.0 percent by weight of the lotion. Preferred surfactants and emulsifiers include primary alkyl sulfates, fatty alkylether sulfates, fatty monoglyceride sulfate, fatty acid peptide condensates, fatty acid-sarcosine condensates, sulfosuccinic acid esters, poly glycosides, phospholipids, linear alkylate sulfonates, and amphoterics, or a combination thereof. The surfactants and emulsifiers generally comprise from about 0.1 to about 10.0 percent by weight of the lotion. Fragrances include those that are currently available on the market which are chemically compatible with the lotion formulation. The fragrances generally comprise from about 0.01 to about 2.0 percent by weight of the lotion. A preferred lotion is the BABY FRESH™ base lotion. It is preferred that the pH of the lotion system be between about 7 and about 9 for use with babies and infants.

For an individual to use the wet wipe without its disintegration in the individual's hand, the wet wipe of the invention must have a sufficient wet strength. The wet strength of the wet wipe can be evaluated by the well known CDLT strength test described in Example 2. The wet wipe wet strength is preferably examined in an aging test at 1 week, 1 month, and 3 months. An acceptable wet wipe possesses a wet strength that has passed a room temperature and 50° C. aged test. After aging in room temperature and 50° C., the wet wipe preferably retains significant cross-directional wet strengths of 8 to 20 oz/in. More preferably, the wet wipe retains cross-directional wet strengths of 12 to 16 oz/in. A typical wet wipe CDLT test is presented in Example 3 herein.

Appropriately sized, the wet wipe is also flushable in normal household toilet systems. The wet wipe of the invention readily disintegrates with agitation in a large volume of water. To analyze dispersibility, which is a measure of flushability, the snag breakup test is preferred. A dispersibility time of less than three minutes is preferred. It is more preferred that the dispersibility time is less than two minutes.

The wet wipes of the present invention are preferably biodegradable. The wet wipes will also be mild such that they can be used for human use without inducing allergic responses or other similar phenomena. The wet wipes preferably pass the repeated insult patch test (RIPT) and other toxicity testing. The wet wipes of the invention are non-toxic to humans.

It is surprising to find a total lotion system that meets the balanced requirements of mildness and strength while retaining the ability to be dispersible. The present invention provides an alkaline wet wipe comprising a gentle lotion system containing low concentrations of boric acid and relatively high levels of sodium bicarbonate, while maintaining strength and dispersibility. This combination of properties is highly desirable.

EXAMPLES

Example 1: The Snag Breakup Test

The snag breakup test can be used to determine the time required to breakup a single wet wipe product. Generally, a stir bar is placed in a beaker that is filled to a depth of six inches with water or a buffer of appropriate pH. The beaker is placed on a magnetic stirrer and the speed is adjusted as desired. The solution is adjusted to the desired testing temperature. The wet wipe sample for testing is wrapped around a steel rod, that is preferably 8 inches long, ⅛ inch in diameter, with a hooked end (about ¼ inch bent at an angle of 110°). The sample preferably does not extend beyond the bent end of the rod. The solution is stirred at a constant velocity and the rod is placed in a clamp attached to a ring stand. The rod is located above the beaker at a point midway between the center and the rim of the beaker. The sample is gently lowered into the solution until the sample is fully submerged. The time is measured until the first piece of any size breaks away from the wet wipe and until the sample breaks free from the steel rod.

Example 2: CDLT Test

The wet strength of wet wipes of varying concentrations of boric acid and sodium bicarbonate were examined by CDLT at room temperature and the results presented in Table 1. The CDLT of a sample wet wipe is preferably tested on an appropriate apparatus such as the Thwing-Albert Intelect II STD Apparatus according to instructions set forth by the manufacturer. The test procedures for determining dry tencel strength of a sample wet wipe are well known by the art skilled and are briefly set forth herein. Five sample strips are placed squarely in the top clamp of the tencel strength apparatus. The clamps are closed and one of the strips hanging from the top clamp is separated and its free end is placed in the bottom clamp. A very light tension is applied to remove the slack and the bottom clamp is applied. The test is then begun according to the instructions set forth by the manufacturer. After the test strip fractures, the test sequence is repeated for the four remaining sample strips. For wet tencel strength, five sample strips are tested. The two ends of the sample strip are placed together to form a loop in the center. The bent loop portion of the sample is placed into the beaker of either distilled water to test unlotionized wet wipes or into a beaker containing the lotion to test lotionized wet wipes. The wet center loop of the sample is gently touched to a towel to remove excess water or lotion and the sample is then inserted into the grips of the apparatus. The dry tencel strength sequence is then performed. As can be seen from Table 1, satisfactory CDLT with very low levels of boric acid concentrations can be achieved. FIGS. 1 and 2 show CDLT values for solutions 1–12 over one month at room temperature (21° C.) and at 52° C., respectively. In addition, the variation of boric acid with bicarbonate is depicted in FIG. 3. Moreover, Table 2 presents wet strength values for wet wipes having various lotion compositions after one week at room temperature. As can be seen, significant strength can be achieved with wet wipes having lotion concentrations of boric acid as low as 0.33% when the sodium bicarbonate concentrations are raised.

TABLE 1

CDLT at Various Concentrations and Aging (oz./in.)

| Soln. No. | Solution Borate/ bicarb/H₂O | 1 Day | 7/8 Days | 2 Wks | 4 Wks | pH | 52° C. 1 wk |
|---|---|---|---|---|---|---|---|
| 1 | 0.99%/1.5%/W | 5.9 | 4.4 | X | X | 7.72 | X |
| 2 | 0.66%/1.5%/W | 6.1 | 4.6 | X | X | 7.85 | X |
| 3 | 0.33%/1.5%/W | 6.9 | 3.7 | X | X | 8.33 | X |
| 4 | 0.99%/4.5%/W | 10.7 | 7.6 | 7.9 | 7.9 | 8.05 | X |
| 5 | 0.66%/4.5%/W | 10.3 | 8.5 | 8.6 | 7.9 | 8.02 | X |
| 6 | 0.33%/4.5%/W | 9.7 | 7.9 | 7.0 | 6.3 | 8.16 | X |
| 7 | 0.99%/7.5%/W | 14.6 | 13.3 | 13.0 | 11.5 | 8.06 | 8.5 |
| 8 | 0.66%/7.5%/W | 13.6 | 12.2 | 12.3 | 11.9 | 8.14 | 6.8 |
| 9 | 0.33%/7.5%/W | 10.7 | 10.2 | 10.1 | 10.3 | 8.14 | 6.4 |
| 10 | 0.9%/10%/W | 15.5 | 15.0 | 14.6 | 11.4 | 7.77 | 11.8 |
| 11 | 0.99%/7.5%/L | 15.8 | 15.2 | 13.2 | 10.8 | 7.83 | 8.1 |
| 12 | 0.9%/7.5%/L | 16.1 | 14.7 | 13.1 | 10.4 | 7.81 | 10.4 |

W = H₂O; L = BABY FRESH ™ Lotion

TABLE 2

CDLT at 7 Days at Room Temperature (oz./in.)

| Boric Acid % | Sodium Bicarbonate % | | | | |
|---|---|---|---|---|---|
| | 1.5 | 4.5 | 5.5 | 6.5 | 7.5 |
| 0.11 | NA | NA | 5.7 | 5.4 | NA |
| 0.33 | 3.7 | 7.9 | 6.5 | 8.4 | 10.2 |
| 0.66 | 4.6 | 8.5 | 10.1 | 9.9 | 12.2 |
| 0.99 | 4.4 | 7.6 | 10.9 | 12.8 | 13.3 |

Example 3: Compositions of Lotion for Wet Wipes

The following lotion solutions are preferred.

| 0.5% Solution | |
|---|---|
| Water | 91.22% |
| Propylene Glycol | 1.50% |
| Cocoamphodiacetate | 0.25% |
| Polysorbate 20 | 0.20% |
| Methyl Paraben | 0.20% |
| Propyl Paraben | 0.03% |
| Sodium bicarbonate | 6.00% |
| Boric acid | 0.50% |
| Suttocide A | 0.1% |
| 0.6% Solution | |
| Water | 91.12% |
| Propylene Glycol | 1.50% |
| Cocoamphodiacetate | 0.25% |
| Polysorbate 20 | 0.20% |
| Methyl Paraben | 0.20% |
| Propyl Paraben | 0.03% |
| Sodium bicarbonate | 6.00% |
| Boric acid | 0.60% |
| Suttocide A | 0.1% |
| 0.7% Solution | |
| Water | 91.02% |
| Propylene Glycol | 1.50% |
| Cocoamphodiacetate | 0.25% |
| Polysorbate 20 | 0.20% |
| Methyl Paraben | 0.20% |
| Propyl Paraben | 0.03% |
| Sodium bicarbonate | 6.00% |
| Boric acid | 0.70% |
| SUTTOCIDE A ™ antimicrobial | 0.1% |

What is claimed is:

1. A pre-moistened, dispersible, biodegradable wet wipe comprising:

a) a web of non-woven fibers and a binder selected from the group consisting of a polyvinyl alcohol, a polymer emulsion stabilized with an aqueous polyvinyl alcohol, a blend of a polyvinyl alcohol and an aqueous polymer emulsion, and a combination thereof;

b) an aqueous lotion comprising: from about 0.1 to about 0.9 percent by weight of the lotion of boric acid; from about 5 to about 8 percent by weight of the lotion of an alkali metal bicarbonate; and a preservative effective for inhibiting microbial activity in said lotion; and c) said wet wipe having a pH between 7 and about 9 and a wet strength between about 8 and about 20 oz/in.

2. The wet wipe of claim 1 in which the amount of the aqueous lotion solution ranges from 100 to 350 percent by weight of the web.

3. The wet wipe of claim 1 in which the boric acid is from about 0.3 to about 0.7 percent by weight of the lotion.

4. The wet wipe of claim 1 in which the alkali metal bicarbonate is from about 6 to about 7 percent by weight of the lotion.

5. The wet wipe of claim 1 in which the boric acid is from about 0.3 to about 0.7 percent by weight of the lotion and the alkali metal bicarbonate is from about 6 to about 7 percent by weight of the solution.

6. The wet wipe of claim 5 in which the wet wipe has a wet strength between about 12 and about 16 oz/in.

7. The wet wipe of claim 1 in which the alkali metal bicarbonate is sodium bicarbonate.

8. The wet wipe of claim 1 wherein the aqueous lotion solution further comprises a moisturizer and a surfactant.

9. The wet wipe of claim 8, wherein the aqueous solution further comprises a fragrance.

10. A pre-moistened, dispersible, biodegradable wet wipe comprising:

a) a web of non-woven fibers and a binder selected from the group consisting of a polyvinyl alcohol, a polymer emulsion stabilized with an aqueous polyvinyl alcohol, a blend of a polyvinyl alcohol and an aqueous polymer emulsion, and a combination thereof;

b) an aqueous lotion comprising: from about 0.3 to about 0.7 percent by weight of the lotion of boric acid; from about 6 to about 7 percent by weight of the lotion of sodium bicarbonate;

c) said lotion further comprising: propylene glycol, cocoamphodiacetate, polysorbate 20, methyl paraben, propyl paraben, and sodium hydroxymethylglycinate effective for inhibiting microbial activity in said lotion; and d) said wet wipe having a pH between 7 and about 9 and a wet strength between about 8 and about 20 oz/in.

* * * * *